United States Patent
Behrens

[11] Patent Number: 6,033,407
[45] Date of Patent: Mar. 7, 2000

[54] APPARATUS AND METHOD FOR INTRAMEDULLARY NAILING AND INTRAMEDULLARY NAIL THEREFOR

[76] Inventor: Alfred F. Behrens, One Harwood Dr., Madison, N.J. 07940-2710

[21] Appl. No.: 09/014,377

[22] Filed: Jan. 27, 1998

[51] Int. Cl.[7] ................................................ A61B 17/56
[52] U.S. Cl. .......................................... 606/62; 606/67
[58] Field of Search ............................ 606/72, 73, 151, 606/232, 185, 170

[56] References Cited

U.S. PATENT DOCUMENTS

| | | |
|---|---|---|
| 1,951,278 | 6/1934 | Ericsson . |
| 2,243,717 | 5/1941 | Moreira . |
| 2,486,136 | 10/1949 | Ericsson . |
| 2,536,296 | 1/1951 | Longfellow . |
| 2,952,254 | 9/1960 | Keating . |
| 3,103,926 | 9/1963 | Cochran et al. . |
| 3,255,747 | 6/1966 | Cochran et al. . |
| 3,255,760 | 6/1966 | Di Cosola . |
| 3,892,232 | 7/1975 | Neufeld . |
| 4,009,712 | 3/1977 | Burstein et al. . |
| 4,040,129 | 8/1977 | Steinemann et al. . |
| 4,147,164 | 4/1979 | Behney ................................. 128/76 |
| 4,263,903 | 4/1981 | Griggs . |
| 4,381,770 | 5/1983 | Neufeld . |
| 4,383,527 | 5/1983 | Asnis et al. . |
| 4,450,835 | 5/1984 | Asnis et al. . |
| 4,484,570 | 11/1984 | Sutter et al. ........................... 128/92 |
| 4,580,563 | 4/1986 | Gross . |
| 4,633,860 | 1/1987 | Korth et al. .......................... 128/305 |
| 4,696,308 | 9/1987 | Meller et al. . |
| 4,787,378 | 11/1988 | Sodhi . |
| 4,950,270 | 8/1990 | Bowman et al ....................... 606/72 |
| 4,969,887 | 11/1990 | Sodhi . |
| 5,122,134 | 6/1992 | Borzone et al. . |
| 5,203,784 | 4/1993 | Ross et al. . |
| 5,211,645 | 5/1993 | Baumgart et al. . |
| 5,697,946 | 12/1997 | Hopper et al. ....................... 606/185 |
| 5,713,901 | 2/1998 | Tock ..................................... 606/92 |
| 5,800,435 | 9/1998 | Errico et al. .......................... 606/61 |
| 5,814,073 | 9/1998 | Bonutti ................................ 606/232 |
| 5,827,285 | 10/1998 | Bramlet ................................. 606/60 |
| 5,865,809 | 2/1999 | Moenning et al. .................. 606/174 |
| 5,865,847 | 2/1999 | Kohrs et al. ........................... 623/17 |

*Primary Examiner*—Michael Buiz
*Assistant Examiner*—Jonathan D. Goldberg
*Attorney, Agent, or Firm*—Arthur Jacob

[57] ABSTRACT

An intramedullary nail is inserted at a selected location within a natural bone and is removed selectively from the location utilizing an access wire which guides a knife for making an access opening of limited size in alignment with the direction in which the intramedullary nail is to be inserted or removed. Cutting tool guides are secured within the access opening, with the aid of trocars, for gaining access to the bone at the location for insertion of the intramedullary nail, and for gaining access to the intramedullary nail for removal of the intramedullary nail. The intramedullary nail includes a hollow shaft with an end plug provided with an alignment hole for engagement with an access wire which guides a knife to the end plug, and a purchase which is protected from calcification and scar tissue during the service life of the intramedullary nail and which is accessed readily for effecting removal and withdrawal of the end plug for ease of removal of the intramedullary nail.

16 Claims, 13 Drawing Sheets

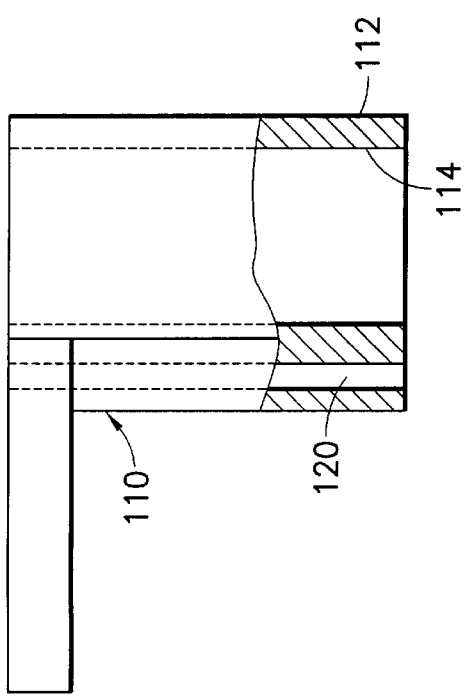
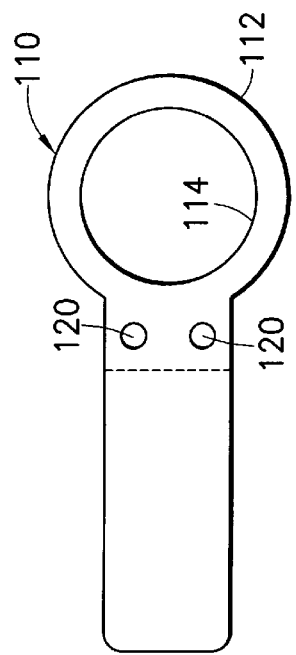
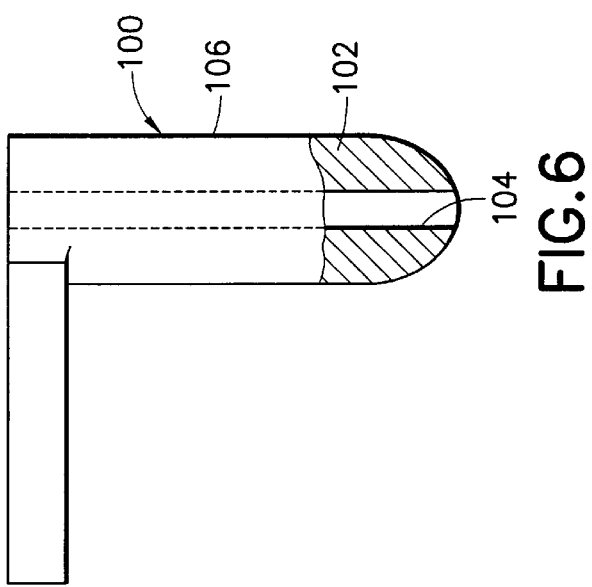
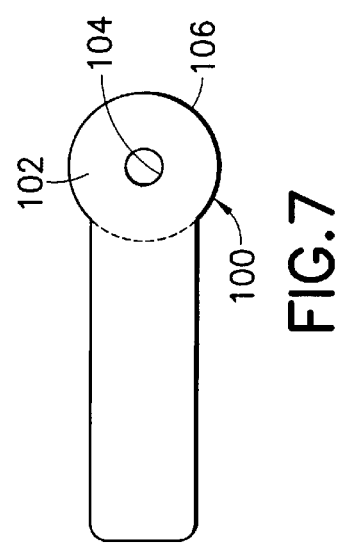

APPARATUS AND METHOD FOR INTRAMEDULLARY NAILING AND INTRAMEDULLARY NAIL THEREFOR

The present invention relates generally to the repair of broken long bones and pertains, more specifically, to the splinting of a fractured long bone with an intramedullary nail.

Efforts to splint a broken bone with a nail inserted into the medullary canal were undertaken as early as the nineteenth century. It was not until much more recently, however, that instrumentation and implants were developed which rendered the method clinically viable, with assured reproducible results. The key components of such recent developments include the use of guide wires for guiding reaming and nail insertion, as well as other elements such as malleable reamers, closed reduction techniques, the use of a traction table, image intensification and, most recently, cross-locking of the nails with screws. Despite continuous improvements, current procedures for insertion and removal of these intramedullary nails still require formal surgical exposure of the nail entry sites. The requirement for surgical exposure leads to added time during nail insertion and removal procedures, with concomitant increases in blood loss, increased length of hospitalization, and resulting scars measuring in length from five to twenty centimeters.

The present invention avoids most of the above-outlined secondary effects of intramedullary nailing procedures by providing apparatus and method, as well as an intramedullary nail, for the percutaneous insertion and removal of an intramedullary nail, requiring skin incisions no longer than about one to two centimeters, thereby reducing the extent of soft tissue dissection, with concomitant significant decreases in hospitalization and recovery times. Rather than relying upon open surgical exposure of the nail entry and exit site, the percutaneous procedures of the present invention accomplish the tasks of nail insertion and removal with the aid of apparatus inserted in alignment with the direction in which the intramedullary nail is to be inserted and removed, and facilitate the aforesaid reduction in the extent of soft tissue dissection. The procedure still relies upon image intensification; however, in most circumstances, eliminates the need for a fracture table, and is adapted for use in connection with the repair of fractures in most long bones.

As such, the present invention attains several objects and advantages, some of which are summarized as follows: Enables the insertion and removal of an intramedullary nail for the treatment of bone fracture and bone reconstruction with reduced soft tissue dissection; provides increased ease and accuracy in the placement of an intramedullary nail and in the subsequent removal of the intramedullary nail; attains a reduction in operating time, decreased blood loss, lessened pain and reduced hospitalization; leaves the patient with a relatively small scar, as opposed to larger scars resulting from current surgical exposure techniques; facilitates the removal of an intramedullary nail when removal is desired; provides reliable and effective treatment of long bone fractures and bone reconstruction, with minimal invasiveness.

The above objects and advantages, as well as further objects and advantages, are attained by the present invention which may be described briefly as an improvement in apparatus for locating and inserting an intramedullary nail at a selected location in a natural bone and along a desired direction through natural soft tissue adjacent the bone at the selected location, the improvement comprising: an elongate, relatively slender access wire having a longitudinally extending axis, a distal end, a securing portion adjacent the distal end and extending along the axis for being secured in the bone at the selected location in the bone, a proximal end, and a guide portion adjacent the proximal end for extending from the bone with the axis extending along the desired direction when the securing portion is secured to the bone; and
a knife having a guideway complementary to the guide portion of the access wire, and a cutting edge oriented relative to the guideway such that upon engagement of the guideway with the guide portion of the access wire and advancement of the knife along the guide portion in the direction of the axis from the proximal end toward the distal end, the cutting edge is moved through the tissue adjacent the bone to provide an access opening extending along the desired direction, through the tissue to the bone at the selected location.

Further, the present invention includes an improvement in a method for locating and inserting an intramedullary nail at a selected location in a natural bone and along a desired direction through natural soft tissue adjacent the bone at the selected location, the improvement comprising: placing and securing an elongate, relatively slender access wire in the bone at the selected location in the bone so as to extend from the bone along the desired direction; engaging a knife with the access wire, the knife having a guideway complementary to the access wire and a cutting edge oriented relative to the guideway such that upon engagement of the knife with the access wire, the access wire is received within the guideway; and advancing the knife along the access wire toward the bone such that the cutting edge is moved through the soft tissue adjacent the bone to provide an access opening extending along the desired direction, through the tissue to the bone at the selected location.

In addition, the present invention provides an intramedullary nail comprising: an elongate hollow shaft extending axially between a proximal end and a distal end; an end plug at the proximal end of the nail, the end plug having a head portion and a shank portion; a fastener fastening the end plug to the shaft for selective axial movement relative to the shaft so as to move at least the head portion of the end plug into and out of the hollow shaft while the shank portion remains within the hollow shaft; and a hole extending axially into the end plug for being accessible by an access wire to align the access wire for guiding a knife to the end plug.

Still further, the present invention includes an improvement in a method for removing an intramedullary nail placed at a location in a natural bone and along a given direction beneath natural soft tissue adjacent the nail at the location, the improvement comprising: placing a relatively slender access wire through the soft tissue to the nail at the location so as to extend from the nail along the given direction; engaging a knife with the access wire, the knife having a guideway complementary to the access wire and a cutting edge oriented relative to the guideway such that upon engagement of the knife with the access wire, the access wire is received within the guideway; and advancing the knife along the access wire toward the nail such that the cutting edge is moved through the soft tissue adjacent the nail to provide an access opening extending through the soft tissue to the nail at the location.

The invention will be understood more fully, while still further objects and advantages will become apparent, in the following detailed description of preferred embodiments of the invention illustrated in the accompanying drawing, in which:

FIG. 6 is side elevational view of a component part shown in FIG. 5;

FIG. 7 is an end view of the component part of FIG. 6;

FIG. 8 is a side elevational view of another component part shown in FIG. 5;

FIG. 9 is an end view of the component part of FIG. 8;

Figure 1:
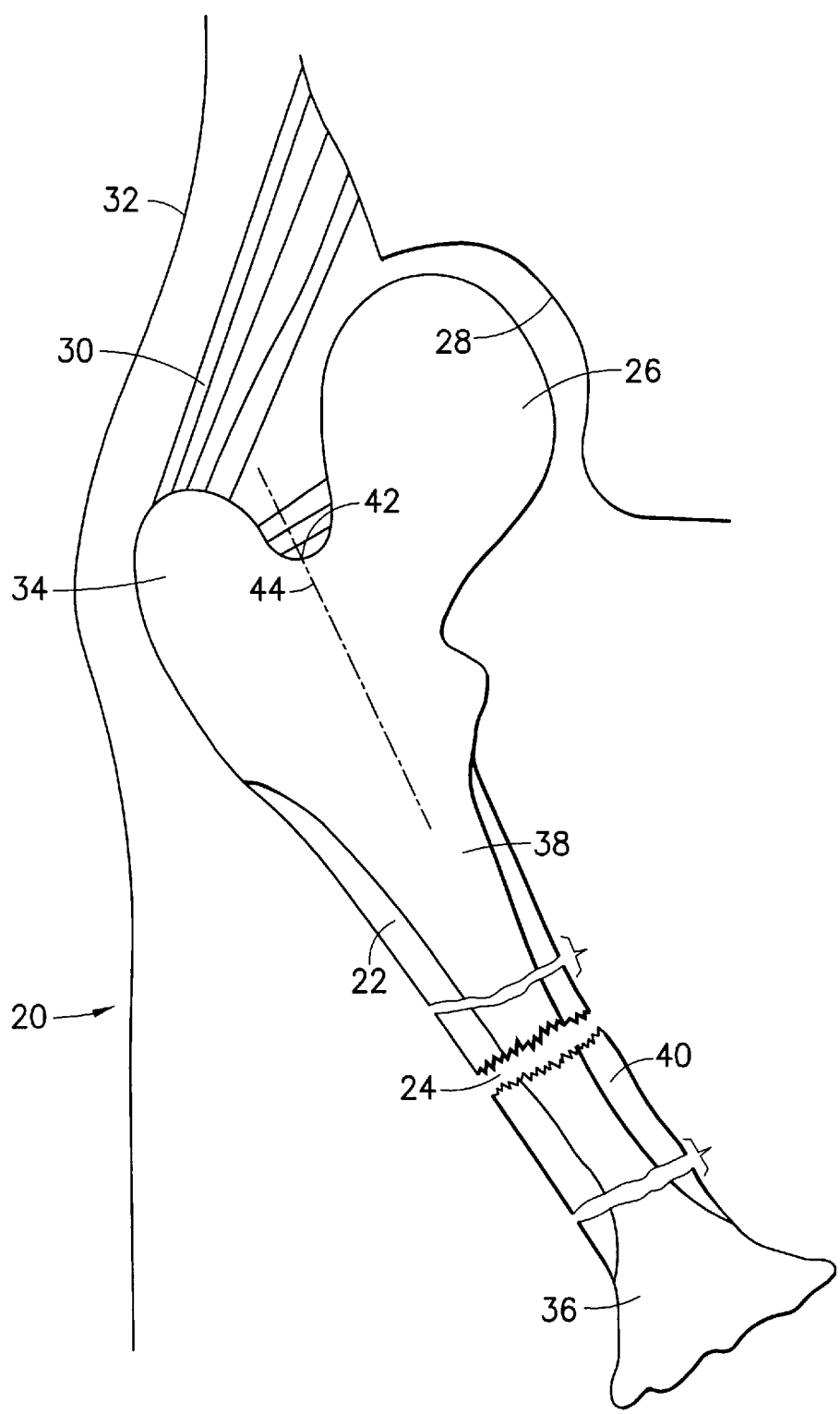
FIG. 1 is a diagrammatic illustration of a long bone fracture site.

Referring now to the drawing, and especially to FIG. 1 thereof, a site of a bone fracture is illustrated generally diagrammatically at 20 and is seen to include a fractured long bone in the form of a femur 22, fractured at 24. Femoral head 26 of femur 22 is seated within acetabulum 28 and the site 20 includes natural soft tissue shown in the form of muscles 30 and skin 32. In order to treat the fracture 24, an intramedullary nail (see FIGS. 13 and 14) is to be inserted into the proximal femur adjacent the greater trochanter 34 and to the distal metaphysis 36 to lock together the proximal and distal portions 38 and 40 of the femur 22. The intramedullary nail is to be located at a selected location 42 in the femur 22 and is to be aligned along a desired direction 44 utilizing apparatus and method of the present invention, as follows.

Figure 2:
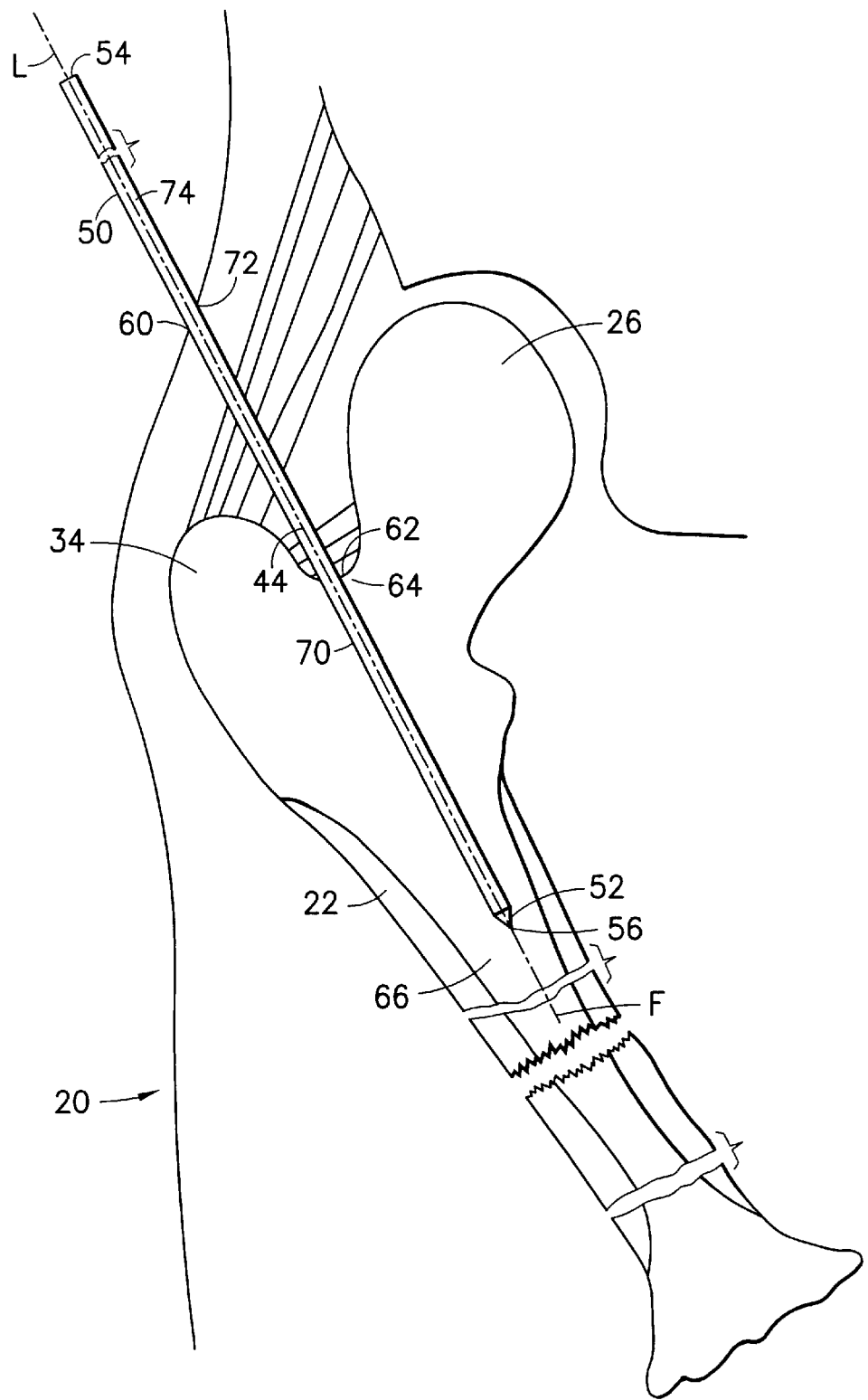
FIG. 2 is a diagrammatic illustration similar to FIG. 1, and showing an initial stage of a procedure of the present invention.

Turning now to FIG. 2, as well as to FIG. 1, an elongate, relatively slender access wire 50 has a longitudinal axis L and extends longitudinally between a distal end 52 and a proximal end 54. Distal end 52 preferably is pointed at 56. Under two-plane fluoroscopy, a one centimeter long lateral skin incision is made in the natural soft tissue at 60, about ten centimeters proximal to the greater trochanter 34 and aligned with femoral axis F. The access wire 50 is inserted through the incision made at 60 and is advanced to the piriformis fossa 62 where the pointed end 56 penetrates the cortex 64 and enters the femoral canal 66, with a distal portion 70 of the access wire 50 providing a securing portion for anchoring the access wire 50 in the natural bone of the femur 22. Since the access wire 50 is quite slender, typically about two millimeters in diameter, the procedure is attained with only minimal soft tissue dissection. Once the access wire 50 is secured in the natural bone, as described, a proximal portion 72 of the access wire 50 extends along the desired direction 44, with the longitudinal axis L of the access wire 50 being aligned with the femoral axis F, the proximal portion 72 having a generally cylindrical outer surface 74 providing a guide portion adjacent the proximal end 54 of the access wire 50, for purposes to be set forth below.

Figures 3, 4:
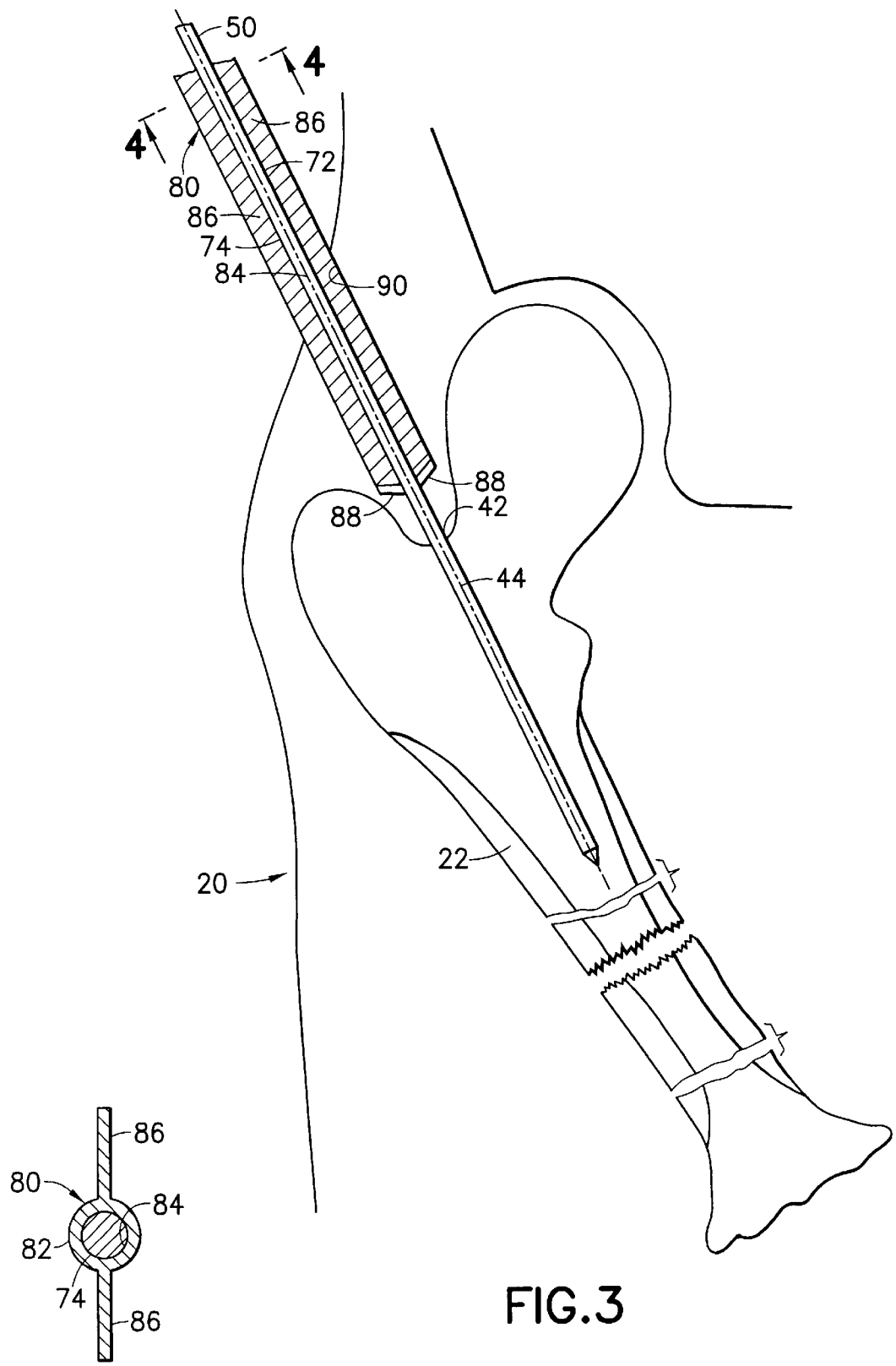
FIG. 3 is a diagrammatic illustration similar to FIG. 2, and showing a further stage of the procedure.
FIG. 4 is an enlarged cross-sectional view taken along line 4—4 of FIG. 3.
Figure 5:
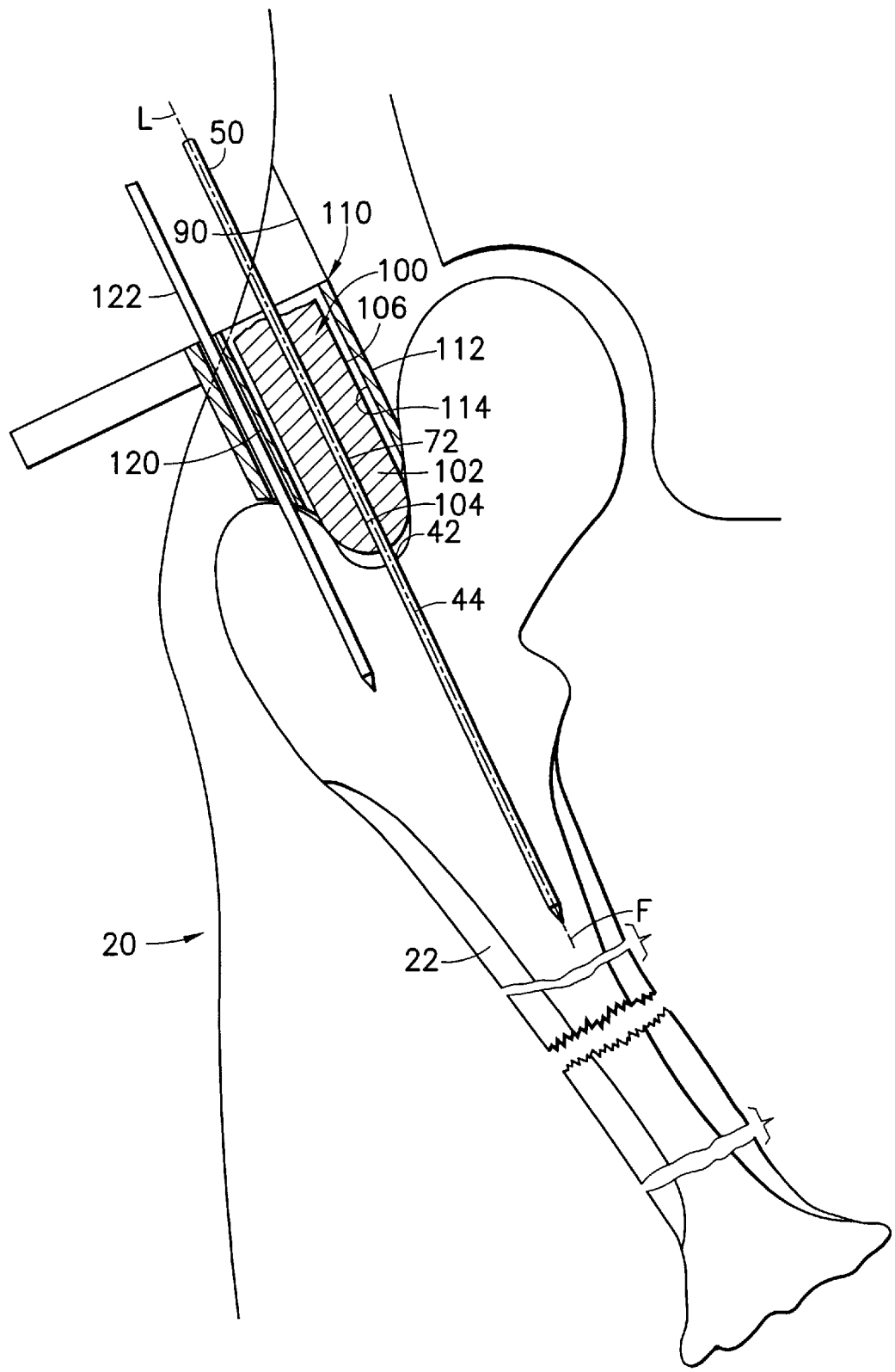
FIG. 5 is a diagrammatic illustration similar to FIG. 3, and showing a still further stage of the procedure.

Referring now to FIGS. 3 and 4, a knife 80 is guided to the selected location 42 at the femur 22, along the desired direction 44, by advancing the knife 80 along the access wire 50 into the soft tissue and toward the bone of the femur 22. To that end, knife 80 includes a longitudinally extending tubular member 82 having a guideway in the form of a generally cylindrical longitudinal bore 84 essentially complementary to the generally cylindrical outer surface 74 of the access wire 50. A pair of blades 86 project laterally from the tubular member 82, in laterally opposite directions, each blade 86 carrying a cutting edge 88 along the forward edge of the blade 86. The access wire 50 is threaded through the knife 80, with the guideway of the knife 80 sliding along the guide portion of the access wire 50, as the knife 80 is advanced along the access wire 50 to the femur 22. In this manner, a relatively small and accurately located incision is made in the soft tissue to provide an access opening 90 extending along the desired direction 44 to the femur 22 at the selected location 42. Typically, the incision is no longer than about one to two centimeters.

Referring now to FIGS. 5 through 9, subsequent to removal of the knife 80 from the access opening 90, a trocar 100 is advanced along the access wire 50 to be seated against the femur 22. Trocar 100 includes a sleeve 102 with a longitudinal passage 104 essentially complementary to the proximal portion 72 of the access wire 50, and an external guide surface in the form of a generally cylindrical outer surface 106. A cutting tool guide 110 includes a bushing 112 extending longitudinally and having an internal guide surface in the form of a generally cylindrical inner surface 114 essentially complementary to the outer surface 106 of the trocar 100. The cutting tool guide 110 is received over the trocar 100 to be placed in the access opening 90, aligned with accuracy with the axes L and F and, consequently, aligned accurately along the desired direction 44 at the selected location 42. Once the cutting tool guide 110 is in place, affixation means in the form of affixation holes 120 receive affixation pins 122 which are driven into the bone of the femur 22 to affix the cutting tool guide 110 in place along the desired direction 44 at the selected location 42.

Figure 10:
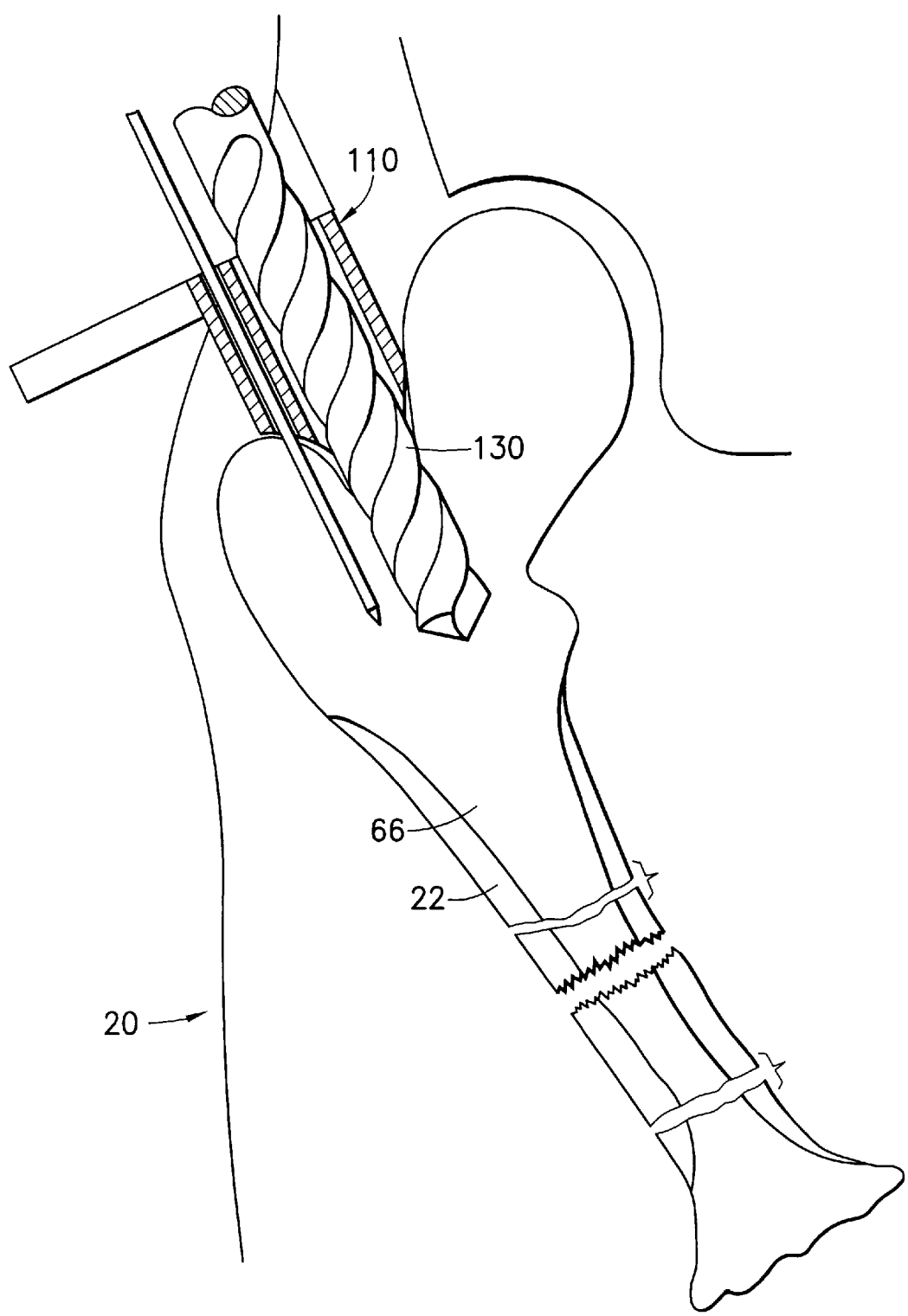
FIG. 10 is a diagrammatic illustration similar to FIG. 1, and showing yet a further stage of the procedure.
Figure 11:
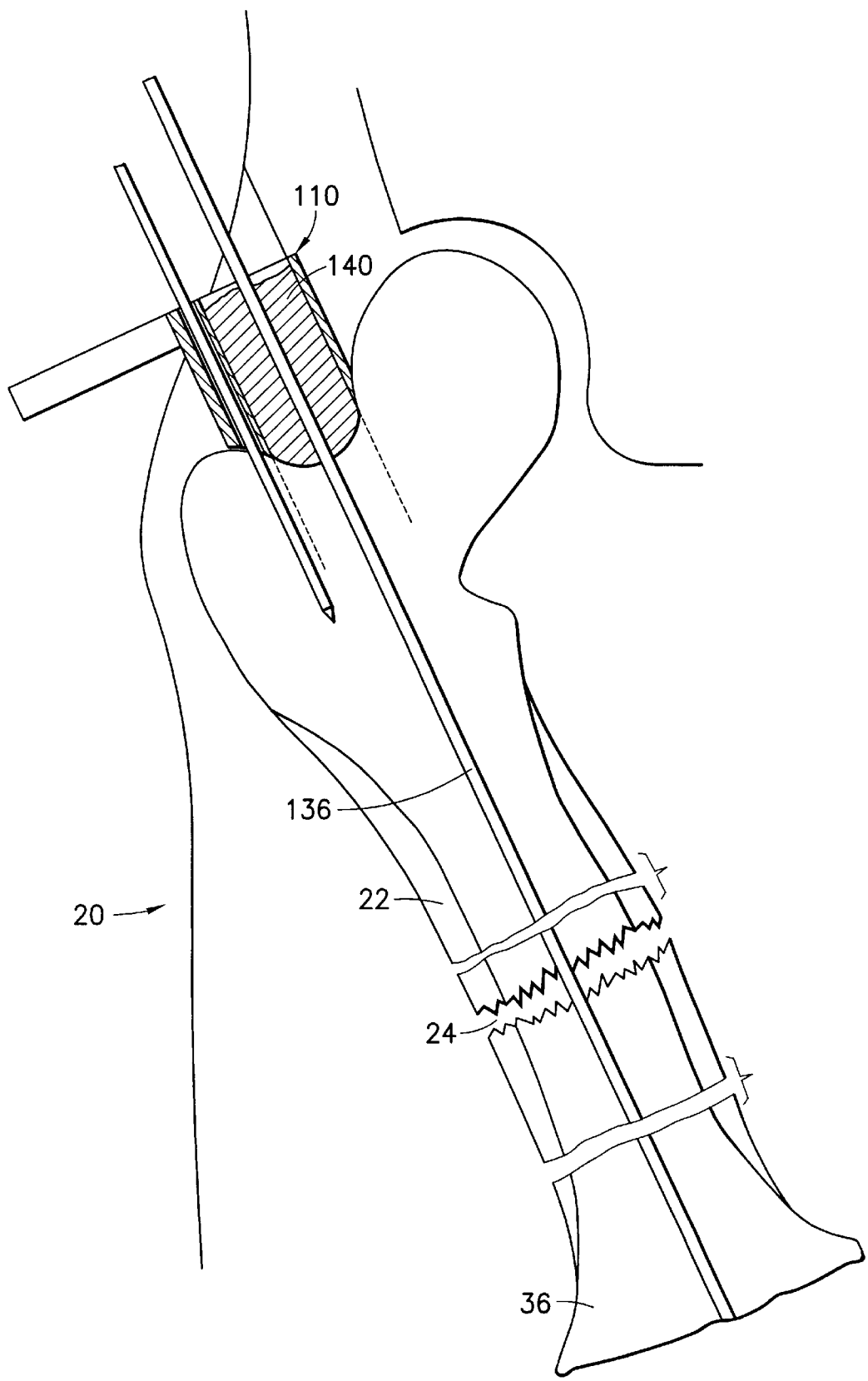
FIG. 11 is a diagrammatic illustration similar to FIG. 1, and showing another stage of the procedure.
Figure 12:
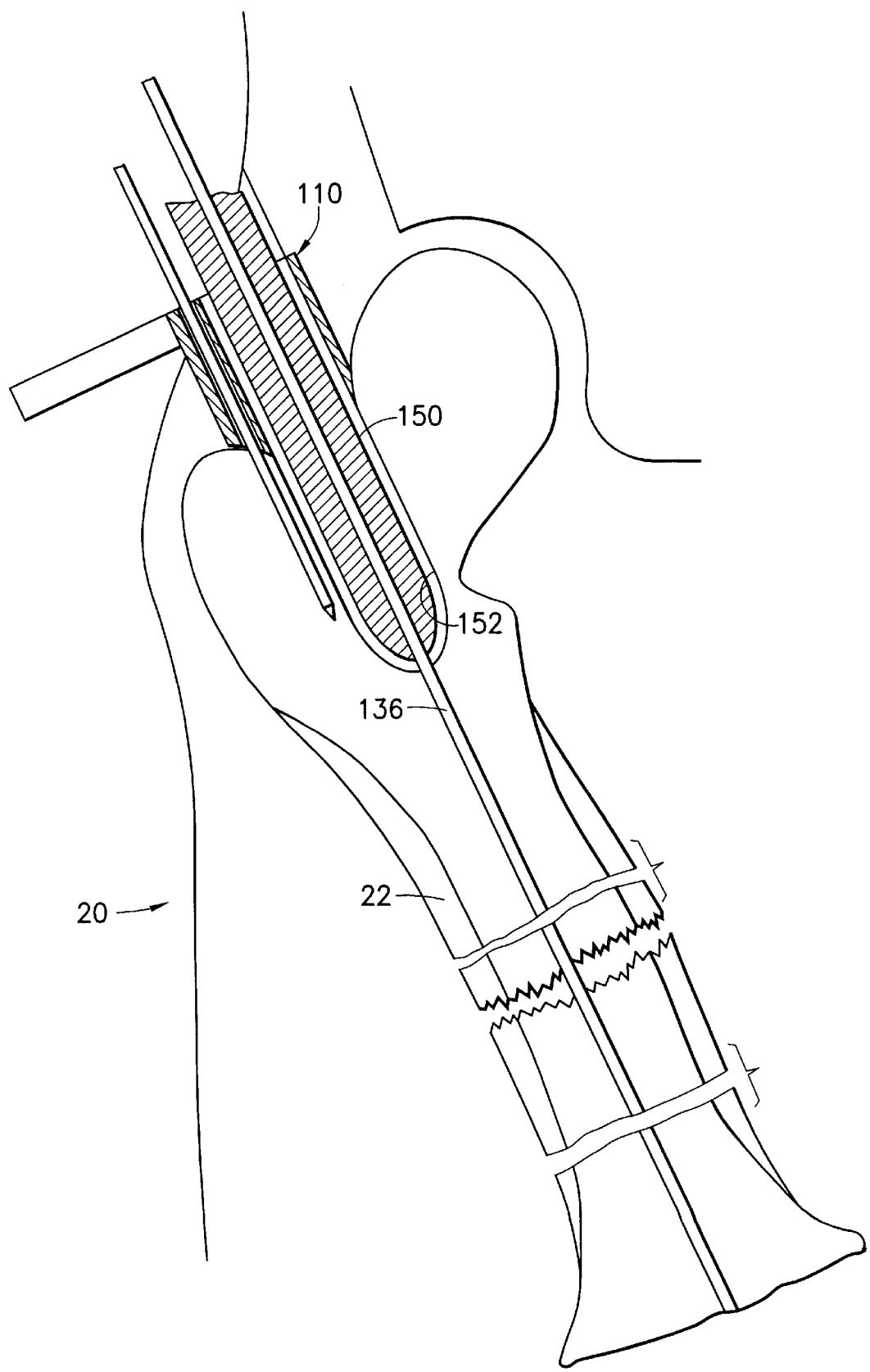
FIG. 12 is a diagrammatic illustration similar to FIG. 1, and showing still another stage of the procedure.
Figure 13:
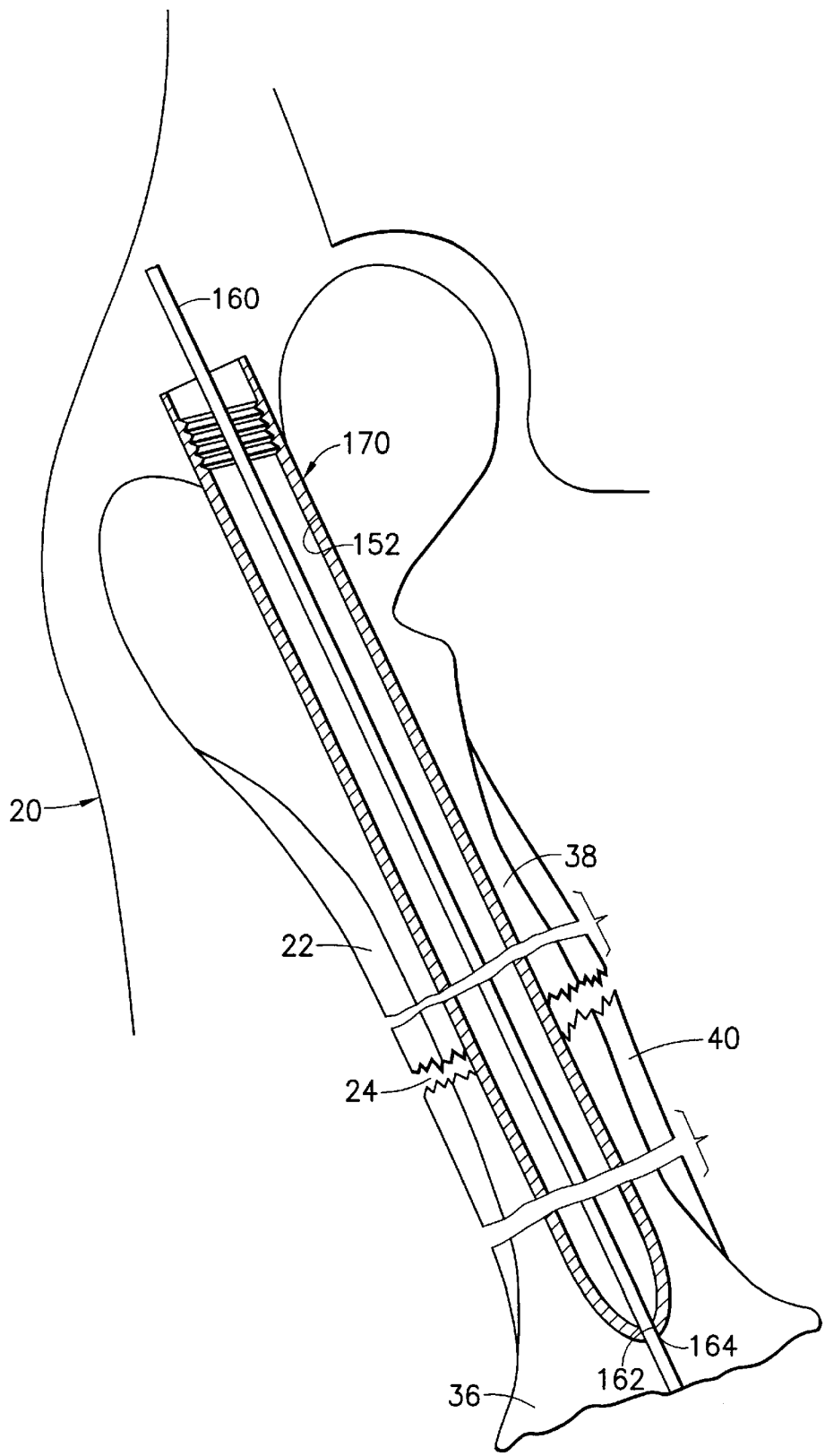
FIG. 13 is a diagrammatic illustration similar to FIG. 1, and showing yet another stage of the procedure.

The trocar 100 then is withdrawn from the cutting tool guide 110, the access wire 50 is removed and, as seen in FIG. 10, a drill 130 is guided by the cutting tool guide 110 and is advanced into the femur 22 to gain access to the femoral canal 66. Alternately, access wire 50 may remain in place and a cannulated drill (not shown) may be guided along the access wire 50. The drill 130 then is removed and a guide wire 136 is inserted to span the fracture 24, the guide wire 136 being guided by a guide wire trocar 140 inserted into the cutting tool guide 110, and being anchored in the distal metaphysis 36, as seen in FIG. 11. The guide wire trocar 140 then is removed and, as seen in FIG. 12, a cannulated reamer 150 is guided by the guide wire 136 to ream a passage 152 of appropriate dimensions and orientation to receive an intramedullary nail. Upon completion of passage 152, guide wire 136 is removed and is replaced by a nail wire 160 (see FIG. 13), with the aid of guide wire trocar 140, which is re-inserted into cutting tool guide 110 for that purpose. Once nail wire 160 is in place, an intramedullary nail 170 is guided by the nail wire 160 into the passage 152 to span the fracture 24 and enter the distal metaphysis 36, the guide wire 160 being threaded through a guide passage 162 at distal end 164 of the intramedullary nail 170, as illustrated in FIG. 13. The nail wire 160 then is removed, and the proximal and distal portions 38 and 40 of the femur 22 are locked together.

Figure 14:
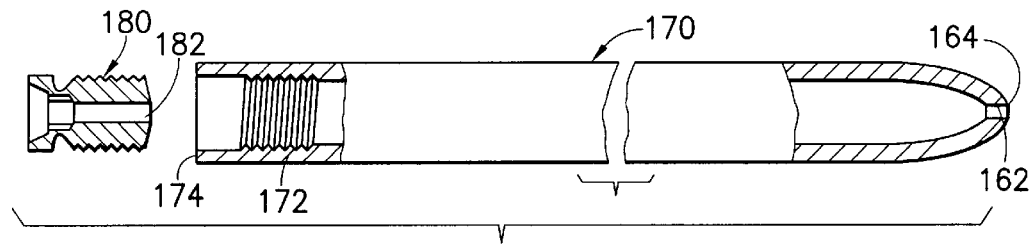
FIG. 14 is a side elevational view of an intramedullary nail constructed in accordance with the invention, exploded and partially sectioned to show internal details.
Figure 15:
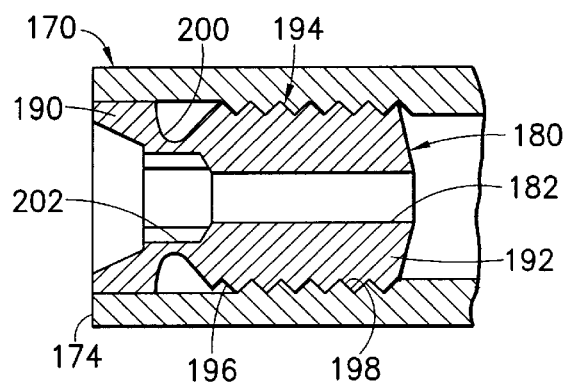
FIG. 15 is an enlarged fragmentary view of a portion of FIG. 14, with component parts assembled.

Turning now to FIGS. 14 and 15, intramedullary nail 170 is seen to include an elongate, hollow shaft 172 extending axially between a proximal end 174 and the distal end 164 of the intramedullary nail 170. An end plug 180 is inserted into the proximal end 174 of the hollow shaft 172 after placement of the intramedullary nail 170, as set forth above. End plug 180 has a head portion 190 and a shank portion 192. A fastener 194 fastens the end plug 180 to the shaft 172 of the intramedullary nail 170 and allows selective axial movement of the end plug 180 relative to the shaft 172, from the retracted position shown in FIG. 15, to an extended position, illustrated in FIG. 19, for purposes described below. In the illustrated preferred construction, fastener 194 includes complementary external and internal screw threads 196 and 198 on the end plug 180 and in the hollow shaft 172, respectively.

When it is desired to remove intramedullary nail 170 from femur 22, the end plug 180 is first removed from the hollow shaft 172, thereby exposing the internal screw thread 198 for coupling with a currently-available threaded pulling tool (not shown) which is then coupled with the hollow shaft 172 and pulled to remove the intramedullary nail 170 from the femur 22. Exposure of the internal screw thread 198 for subsequent removal of the intramedullary nail 170 is facilitated by the construction of the end plug 180. In particular, the end plug 180 includes a hole shown in the form of a guide passage 182, and a purchase on the head portion 190, the purchase being illustrated in the form of an annular groove 200 in the head portion 190 of the end plug 180. Further, a wrenching configuration, shown in the form of a hexagonal socket 202, is located in the head portion 190, in alignment with the guide passage 182. A frusto-conical lead-in surface 204 is located adjacent the socket 202.

Figure 16:
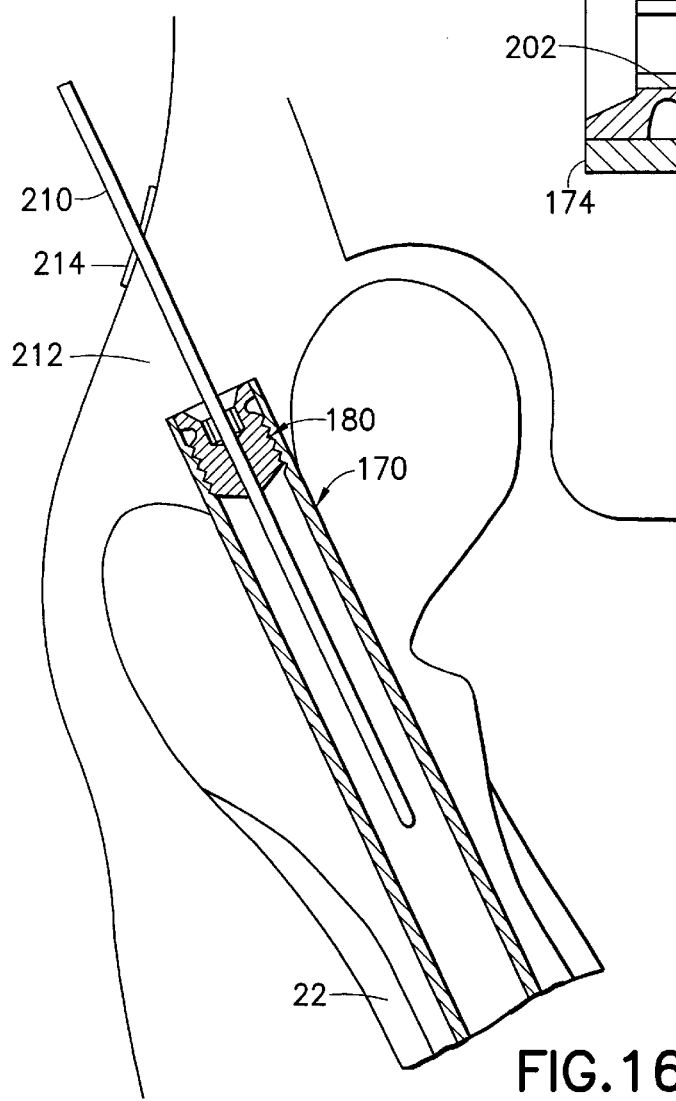
FIG. 16 is a diagrammatic illustration similar to FIG. 1, and showing an initial stage of another procedure conducted in accordance with the present invention.
Figure 17:
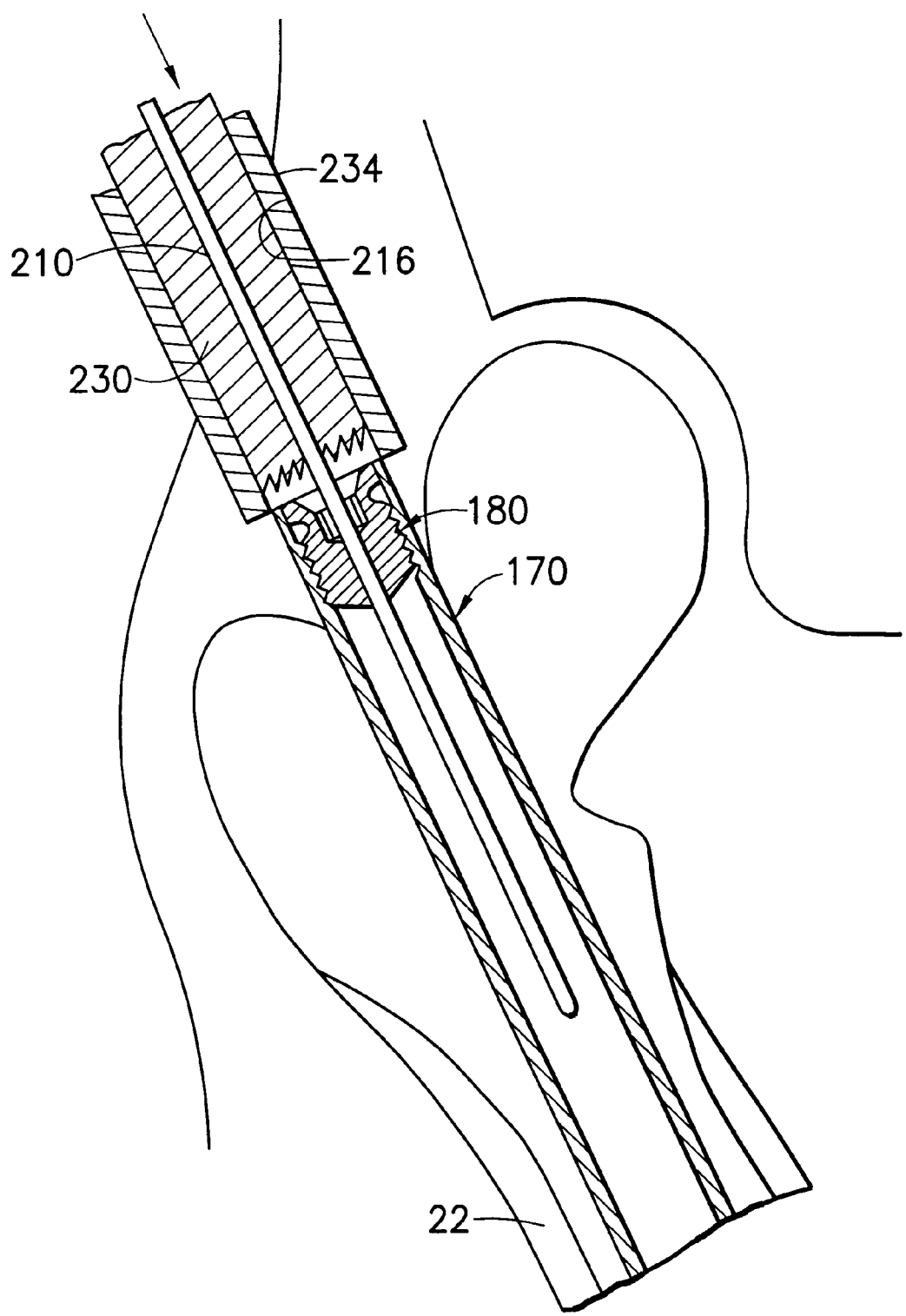
FIG. 17 is a diagrammatic illustration similar to FIG. 16, and showing another stage of the procedure.
Figure 18:
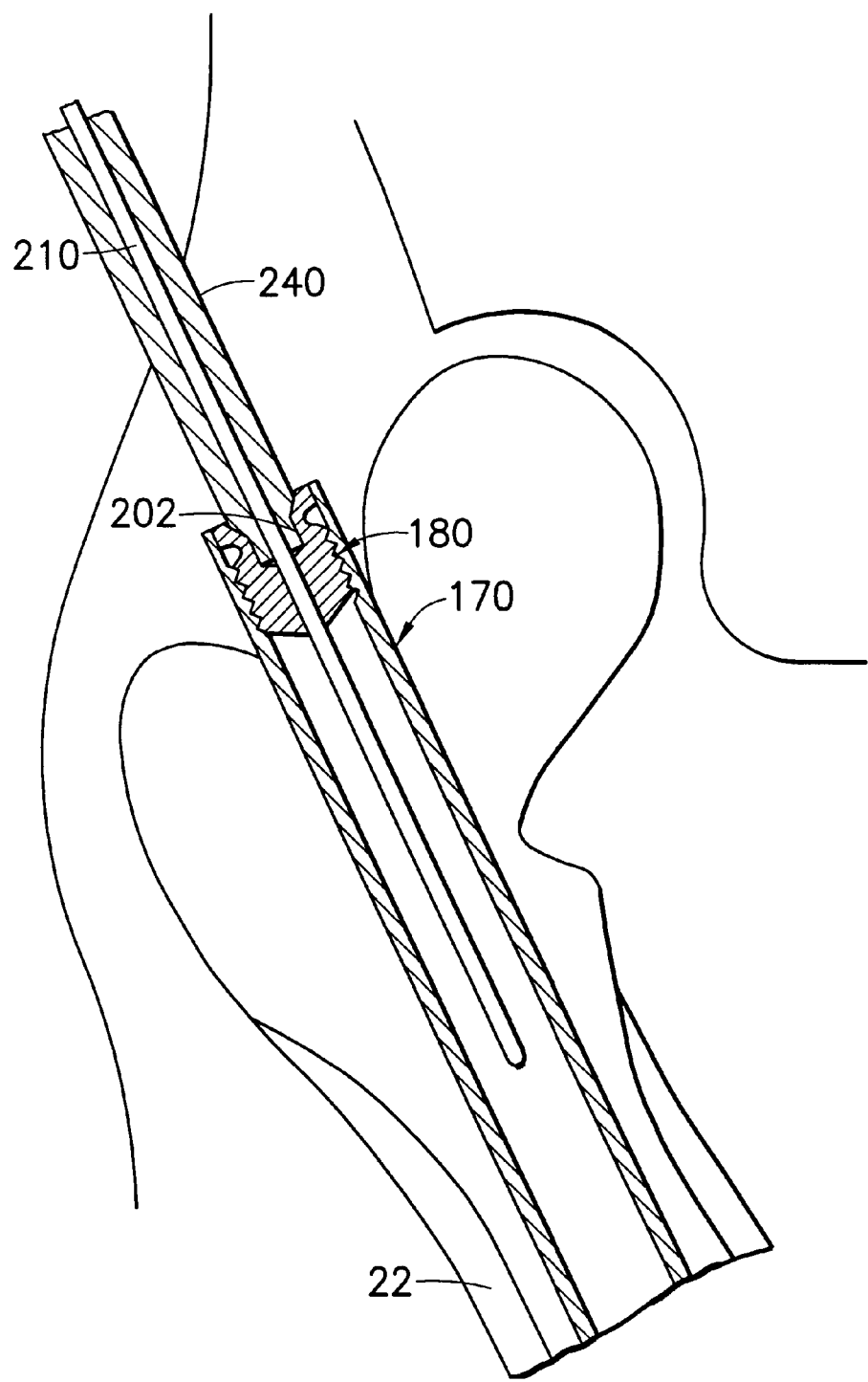
FIG. 18 is a diagrammatic illustration similar to FIG. 16, and showing a further stage of the procedure.
Figure 19:
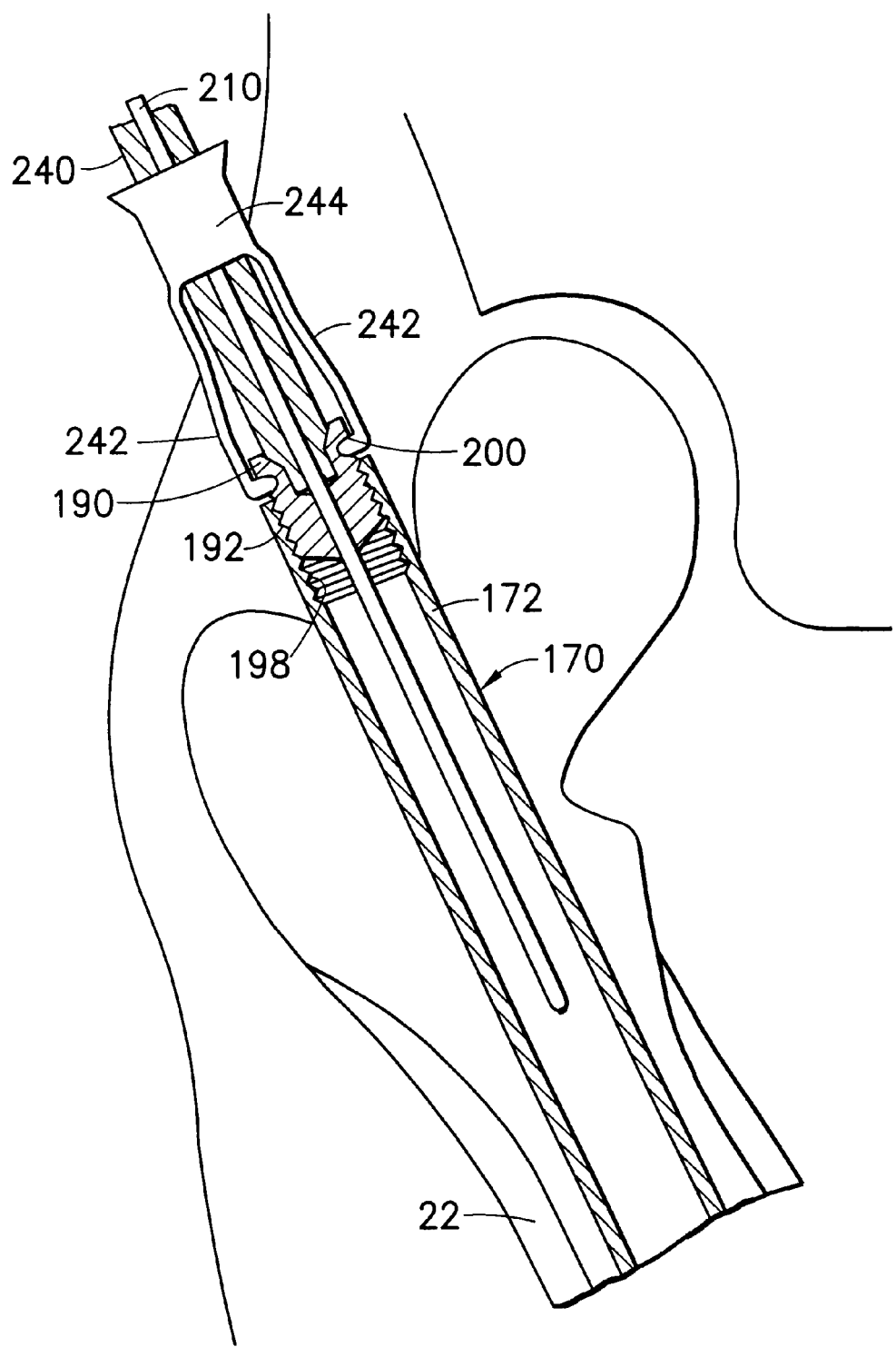
FIG. 19 is a diagrammatic illustration similar to FIG. 17, and showing a still further stage of the procedure.

Referring now to FIGS. 16 and 17, removal of the end plug 180 is accomplished with minimal dissection of the surrounding natural soft tissue by first inserting an access wire 210, under image intensification, through the soft tissue 212 adjacent the end plug 180 and into the guide passage 182, the insertion of access wire 210 into the guide passage 182 being facilitated by the lead-in surface 204. Starting at scar tissue 214, a small incision 216 is made by a guided knife, guided by the access wire 210, as described above in connection with knife 80 and access wire 50, to establish an access opening 216. A cannulated end cutting drill 230 then is guided by the access wire 210 through the soft tissue 212 to clear away any calcification and connective scar tissue for attaining clear access to the end plug 180. Optionally, a cutting tool bushing 234 may be inserted into access opening 216 prior to the use of end cutting drill 230 to protect the surrounding soft tissue 214 as the end cutting drill 230 clears the area adjacent the end plug 180. Then the cutting tool bushing 234, if present, is removed and, as seen in FIG. 18, a cannulated hexagonal driver 240 is guided by the access wire 210 to the hexagonal socket 202 in the end plug 180, the driver 240 is engaged with the socket 202, and the end plug 180 is turned, thereby moving the end plug 180 axially from the retracted position to the extended position where the annular groove 200 is exposed, as seen in FIG. 19. The annular groove 200, having been located inside the hollow shaft 172 of the intramedullary nail 170, is free of any calcification or scar tissue and is immediately available for grasping with the fingers 242 of a grasping tool 244 attached to the driver 240.

Note that the shank portion 192 of the end plug 180 remains threaded into the hollow shaft 172 while the grasping tool 244 is engaged with the head portion 190 of the end plug 180, thereby assisting in effecting the purchase of the fingers 242 on the end plug 180. Continued rotation of the driver 240, and the end plug 180, completes the removal of the end plug 180 from the hollow shaft 172, and the coupling of the grasping tool 244 with the end plug 180 assures that the end plug 180 is removed fully through the access opening 216, leaving the internal thread 198 exposed for engagement with a standard pulling tool (not shown) and subsequent removal of the intramedullary nail 170. Thus, end plug 180 serves to protect the internal thread 198 against calcification or other deterioration during the service life of the intramedullary nail 170, and preserves the internal thread 198 for immediate use in connection with a pulling tool when removal of the intramedullary nail 170 is to be accomplished. Likewise, the purchase provided by the annular groove 200 is protected so as to be available immediately upon extension of the end plug 180 from the hollow shaft 172. Accordingly, access to the end plug 180, for removal as set forth above, is attained with minimal invasiveness through the use of access wire 210 and a guided knife, just as minimal invasiveness is achieved during insertion of the intramedullary nail 170, utilizing access wire 50 and guided knife 80. Once the intramedullary nail 170 is removed, the wound is closed.

It will be seen that the present invention attains the several objects and advantages summarized above, namely: Enables the insertion and removal of an intramedullary nail for the treatment of bone fracture with reduced soft tissue dissection; provides increased ease and accuracy in the placement of an intramedullary nail and in the subsequent removal of the intramedullary nail; attains a reduction in operating time, decreased blood loss, lessened pain and reduced hospitalization; leaves the patient with a relatively small scar, as opposed to larger scars resulting from current surgical exposure techniques; facilitates the removal of an intramedullary nail when removal is desired; provides reliable and effective treatment of long bone fractures, with minimal invasiveness.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An improvement in apparatus for the percutaneous location and insertion of an intramedullary nail at a selected location in a natural bone and along a desired direction through natural soft tissue adjacent the bone at the selected location, the improvement comprising:

an elongate, relatively slender access wire having a longitudinally extending axis, a distal end, a securing portion adjacent the distal end and extending along the axis for being secured in the bone at the selected location in the bone, a proximal end, and a guide portion adjacent the proximal end for extending from the bone with the axis extending along the desired direction when the securing portion is secured to the bone; and a knife having a guideway slidably engageable with the guide portion of the access wire, and a cutting edge oriented relative to the guideway such that upon engagement of the guideway with the guide portion of the access wire and advancement of the knife along the guide portion in the direction of the axis from the proximal end toward the distal end, the cutting edge is moved through the tissue adjacent the bone to provide an access opening extending along the desired direction, through the tissue to the bone at the selected location;

the knife including a longitudinally extending tubular member and at least one blade extending from the tubular member in a lateral direction, laterally beyond the tubular member, the guideway being located on the tubular member and the cutting edge being located on the blade so as to create an incision in the natural soft tissue corresponding to the lateral extent of the blade of the knife.

2. The improvement of claim 1 wherein the guide portion of the access wire includes a generally cylindrical outer surface, and the guideway of the knife includes a generally cylindrical bore for slidably receiving to the outer surface of the guide portion.

3. The improvement of claim 1 wherein the knife includes a pair of blades extending from the tubular member in laterally opposite directions, each blade extending laterally beyond the tubular member, the guideway being located on the tubular member and the cutting edge being located on the blades.

4. The improvement of claim 3 wherein the guide portion of the access wire includes a generally cylindrical outer surface, and the guideway of the knife includes a generally cylindrical bore for slidably receiving to the outer surface of the guide portion.

5. The improvement of claim 1 including:

a trocar having a longitudinal passage for slidable reception of the guide portion and advancement of the trocar along the guide portion into the access opening subsequent to removal of the knife from the opening, the trocar including an external guide surface; and a cutting tool guide having an internal guide surface for guiding a cutting tool for cutting a passage in the bone for the intramedullary nail, the internal guide surface being slidably engageable with the external guide surface of the trocar and extending longitudinally along the cutting tool guide for reception of the cutting tool guide over the trocar and into the access opening to place the cutting tool guide along the desired direction at the selected location, and affixation means on the cutting tool guide for affixing the cutting tool guide to the bone at the selected location, with the internal guide surface extending longitudinally along the desired direction.

6. The improvement of claim 1 including an intramedullary nail comprising:

an elongate hollow shaft extending axially between a proximal end and a distal end;

an end plug at the proximal end of the nail, the end plug having a head portion and a shank portion;

a fastener fastening the end plug to the shaft for selective axial movement relative to the shaft so as to move at least the head portion of the end plug into and out of the hollow shaft while the shank portion remains within the hollow shaft; and a hole extending axially into the end plug for being accessible by an access wire to align the access wire for guiding a knife to the end plug.

7. The improvement of claim 6 including a purchase on the head portion of the end plug, the purchase being retracted within the hollow shaft when the head portion of the end plug is moved into the hollow shaft and being extended axially for enabling grasping of the end plug when the head portion is out of the hollow shaft so as to enable selective removal of the end plug form the hollow shaft, the fastener including a coupling between the end plug and the hollow shaft for holding the end plug in place while the head portion is being grasped for removal of the end plug from the hollow shaft.

8. An improvement in a method for the percutaneous location and insertion of an intramedullary nail at a selected location in a natural bone and along a desired direction through natural soft tissue adjacent the bone at the selected location, the improvement comprising:

placing and securing an elongate, relatively slender access wire in the bone at the selected location in the bone so as to extend from the bone along the desired direction;

engaging a knife with the access wire, the knife having a guideway slidably engageable with the access wire and a cutting edge oriented relative to the guideway such that upon engagement of the knife with the access wire, the access wire is received within the guideway; and advancing the knife along the access wire toward the bone such that the cutting edge is moved through the soft tissue adjacent the bone to provide an access opening extending along the desired direction, through the tissue to the bone at the selected location.

9. The improvement of claim 8 including guiding a cutting tool along the access wire and through the access opening to cut a passage in the bone for insertion of the intramedullary nail along the desired direction at the selected location.

10. An intramedullary nail comprising:

an elongate hollow shaft extending axially between a proximal end and a distal end;

an end plug at the proximal end of the nail, the end plug having a head portion and a shank portion;

a fastener fastening the end plug to the shaft for selective axial movement relative to the shaft so as to move at least the head portion of the end plug into and out of the hollow shaft while the shank portion remains within the hollow shaft;

a hole extending axially into the end plug for being accessible by an access wire to align the access wire for guiding a knife to the end plug; and a purchase on the head portion of the end plug, the purchase being retracted within the hollow shaft when the head portion of the end plug is moved into the hollow shaft and being extended axially for enabling grasping of the end plug when the head portion is out of the hollow shaft so as to enable selective removal of the end plug from the hollow shaft, the fastener including a coupling between the end plug and the hollow shaft for holding the end plug in place while the head portion is being grasped for removal of the end plug from the hollow shaft.

11. The invention of claim 10 wherein the fastener includes complementary screw threads on the end plug and in the hollow shaft for threaded engagement during movement of the head portion of the end plug into and out of the hollow shaft.

12. The invention of claim 11 wherein the coupling includes an extension of the complementary screw threads along the shank portion of the end plug and within the hollow shaft.

13. The invention of claim 11 wherein the purchase includes a groove extending radially into the end plug adjacent the head portion of the end plug.

14. An improvement in a method for the percutaneous removal of an intramedullary nail placed at a location in a natural bone and along a given direction beneath natural soft tissue adjacent the nail at the location, the improvement comprising:

placing a relatively slender access wire through the soft tissue to the nail at the location so as to extend from the nail along the given direction;

engaging a knife with the access wire, the knife having a guideway slidably engageable with the access wire and a cutting edge oriented relative to the guideway such that upon engagement of the knife with the access wire, the access wire is received within the guideway; and advancing the knife along the access wire toward the nail such that the cutting edge is moved through the soft tissue adjacent the nail to provide an access opening extending through the soft tissue to the nail at the location.

15. The improvement of claim 13 wherein the intramedullary nail includes an elongate hollow shaft extending axially between a proximal end and a distal end, an end plug at the proximal end of the nail, the end plug having a hole generally complementary to the access wire and extending axially into the end plug, and the method includes inserting the access wire into the hole upon placing the access wire through the soft tissue to the nail so as to align the access wire and, consequently, the access opening with the nail.

16. The improvement of claim 14 wherein the end plug has a head portion and a shank portion, a fastener fastening the end plug to the shaft for selective axial movement relative to the shaft so as to enable movement of at least the head portion of the end plug into and out of the hollow shaft while the shank portion remains within the hollow shaft, and a purchase on the head portion of the end plug, the purchase being retracted within the hollow shaft when the head portion of the end plug is moved into the hollow shaft and being extended axially for enabling grasping of the plug when the head portion is out of the hollow shaft so as to enable selective removal of the end plug from the hollow shaft, the fastener including a coupling between the end plug and the hollow shaft for holding the end plug in place while the head portion is being grasped for removal of the end plug from the hollow shaft, the method including:

extending the head portion of the end plug to expose the purchase for grasping; and grasping the head portion at the purchase for removing the end plug from the hollow shaft and withdrawing the end plug from the location.

* * * * *